US006517501B1

United States Patent
Slautterback (10) Patent No.: US 6,517,501 B1
(45) Date of Patent: Feb. 11, 2003

(54) CARPAL TUNNEL DEVICE AND METHOD

(75) Inventor: Ernest Gerald Slautterback, Coralsprings, FL (US)

(73) Assignee: FLA Orthopedics, Inc., Miramar, FL (US)

( * ) Notice: Subject to any disclaimer, the term of this patent is extended or adjusted under 35 U.S.C. 154(b) by 71 days.

(21) Appl. No.: 09/677,210

(22) Filed: Oct. 2, 2000

(51) Int. Cl.[7] .................................................. A61F 5/00
(52) U.S. Cl. ............................... 602/5; 602/20; 602/21
(58) Field of Search .......................... 602/5, 6, 12, 20, 602/21, 22, 60, 61, 62, 63, 64; 128/877–880; 2/16, 20, 21

(56) References Cited

U.S. PATENT DOCUMENTS

| | | | |
|---|---|---|---|
| 4,479,648 A | * 10/1984 | Alivo, Jr. ........................ | 2/170 |
| 4,531,241 A | 7/1985 | Berger | |
| 4,850,341 A | 7/1989 | Fabry et al. | |
| 4,854,309 A | * 8/1989 | Elsey ........................... | 602/21 |
| 5,160,314 A | 11/1992 | Peters | |
| 5,214,799 A | 6/1993 | Fabry | |
| 5,267,943 A | * 12/1993 | Dancyger ..................... | 602/20 |
| 5,368,550 A | * 11/1994 | Sisley .......................... | 602/21 |
| 5,385,537 A | 1/1995 | Davini | |
| 5,417,645 A | 5/1995 | Lemmen | |
| 5,468,220 A | 11/1995 | Sucher | |
| 5,746,707 A | 5/1998 | Eck | |
| 5,769,804 A | 6/1998 | Harris et al. | |
| 6,196,985 B1 | * 3/2001 | Slautterback ................ | 128/880 |
| 6,213,969 B1 | * 4/2001 | MacMorran et al. .......... | 602/21 |

* cited by examiner

Primary Examiner—Michael A. Brown
Assistant Examiner—Quang D Thanh
(74) Attorney, Agent, or Firm—Dougherty & Clements LLP (57) ABSTRACT

A user wearable wrist support formed of low temperature moldable, formable plastic, normally closed-cell foam laminated between surface sheets of fabric. The wrist support comprises a curvate clasp having a generally self-supporting C shaped cross section, with the clasp encircling the wrist of the wearer. The clasp is secured in position by a strap. A palmar stay extends transverse of the clasp onto a palmar pad integrally extending from a side of the clasp. In one embodiment the clasp is provided with outwardly extending wrist support rests alongside the stay for supporting the clasp on a planar surface. In another embodiment the support comprises two sheets of plastic material of different densities and hardness sandwiching and embedding a stay therebetween. The device is fabricated by first creating a sheet of foam laminated with at least one surface fabric sheet. Blanks for forming the clasp are cut from the foam sheet and subjected to selective compression, heat, and molding to form the support. The compression heat and molding create a clasp having a generally self-supporting C-shaped cross section which receives the wrist of a wearer, and is secured in position by a releasable strap. With the two layer version of the support, the outer layer is formed in the same manner, the stay is positioned, and the inner soft foam layer is then attached.

15 Claims, 6 Drawing Sheets

CARPAL TUNNEL DEVICE AND METHOD

FIELD OF THE INVENTION

The present invention is directed to a wrist support useful in combating the effects known as Carpal Tunnel Syndrome, and the method of making the same.

BACKGROUND OF THE INVENTION

Carpal tunnel syndrome is a well known, commonly occurring hand condition, sometimes referred to as median compression neuropathy within the carpal canal. The most common symptoms of this condition include intermittent pain and numbness of the hand. Such pain or numbness results from compression of the median nerve which extends from the wrist centrally into the palm of the hand between the palm heel and the ball of the thumb. In carpal tunnel syndrome, a dense fibrous tissue called the transverse carpal ligament forms over the median nerve and compresses it, producing the symptoms of pain and numbness.

Treatment of carpal tunnel syndrome varies according to the severity of the condition. Severe conditions usually require hand surgery to sever the transverse carpal ligament. For less severe cases, the use of a splint which immobilizes the wrist is sometimes effective, often in combination with an anti-inflammatory medication. Such treatments are generally expensive, painful, and may reduce the patient's ability to use the affected hand.

Carpal tunnel syndrome is a particular problem for workers in industries which require repeated manual operations with a held implement or tool. In many such industries it is a leading cause of workmen's compensation claims.

Many different devices have been proposed for treating or preventing carpal tunnel syndrome. For example, protective gloves have been proposed as one means of preventing carpal tunnel syndrome due to wrist flexing. Berger U.S. Pat. No. 4,531,241 issued Jul. 30, 1985, describes a glove having a pad which covers the palm, wrist and a portion of the forearm. The glove restricts free action of the wrist. Fabry et al., U.S. Pat. No. 4,850,341 issued Jul. 25, 1989, describes a glove with a tapered pad designed for use by meat cutters or others using an implement with an action similar to using a knife. While this glove is useful for some applications, its pad configuration is not convenient for other types of actions in which the palm bends, particularly across the central fold of the hand. Fabry U.S. Pat. No. 5,214,799 issued Jun. 1, 1993, describes a glove for preventing carpal tunnel syndrome which has palm-covering padding to protect the wearer's hand. The padding is made of a resilient flexible material such as foam rubber intended to provide protection from vibrations and shocks. The padding has a fold line extending diagonally across the palm to facilitate gripping the handle of an implement. All of these glove type braces and supports have the effect of unduly restricting the motion of the wearer's hand.

Modern day keyboarding is a commonplace and widespread activity which is associated with Carpal Tunnel Syndrome, which is also referred to as Repetitive Motion Trauma. In response to this problem keyboard wrist rests and wrist supports have become ubiquitous. Keyboard wrist rests are manufactured in various widths for use with calculators, computer keyboards, typewriters and the like. These keyboard wrist rests are intended to keep the hands and wrists at a 15 degree angle, which is referred to as the neutral position.

Another type of wrist supports which are used may be classified as sewn orthopedic wrist supports or braces. These devices more or less encase the wrist and at least a portion of the hand. They are manufactured in various colors and provide three levels of support, light, medium and heavy. Those which are intended to provide light or medium support include elastic or neoprene material with a thumbhole. The material wraps around the hand and wrist and is fastened with a hook and loop closure. Products for providing heavy support more closely resemble a brace, using plastic or metal strips called "stays" as the means to obtain the rigidity necessary to stabilize and position the hand and wrist joint. It is uncomfortable to wear most such devices for keyboarding.

Still other devices which have been proposed for treating carpal tunnel syndrome include pull on supports or braces, plastic or metal splints secured by straps, bracelet like appliances, laced immobilizing braces, and wrist braces.

Peters U.S. Pat. No. 5,160,314 issued Nov. 3, 1992, describes a unitary body support adapted to be pulled onto and positioned about the hand and wrist area and adapted to anatomically conform to the wrist and basal hand of the wearer. The brace comprises a sleeve constructed of a resilient elasticized fabric including an outer layer having a brushed looped texture. The sleeve is provided with a thumb opening and means for receiving a removable palmar stabilizing stay. The sleeve includes an integral compression strap which is sufficiently long to extend around the wrist at least once, and which is provided at its free end with hook attachment means for releasable engagement with the outer fabric loops.

Lemmen U.S. Pat. No. 5,417,645 issued May 23, 1995, describes an elongated flexible plastic or metal splint which extends from the center of the palm upwards along the wrist. It is secured in position by wrist and palmar strapping.

Eck U.S. Pat. No. 5,746,707 issued May 5, 1998 describes a wrist and two digit restraining device comprising a rigid metal or plastic splint element which receives the wrist, extends to support the heel and palm of the hand, and terminates at the base of the second, third and fourth fingers. Attachment straps are provided for the wrist support, thumb support and finger support. The device imposes a degree of restraint which would preclude keyboarding and many other activities.

Sucher U.S. Pat. No. 5,468,220 issued Nov. 21, 1995 describes a bracelet-like appliance which comprises a C-shaped member having a central portion located over the dorsal side of the wrist and two arms encircling the wrist. Each arm has a pad for engaging the palm near the attachment edges of the carpal ligament at the medial border and the lateral border of the carpal bones. The bracelet also includes a pad attached to the central portion for engaging the dorsal part of the wrist. The member is shaped to cause the pad attached to the central portion to press against the dorsal side of the wrist while the ends of each arm press in the opposite direction on the edges of the palm. The C-shaped member is a single piece of resilient, malleable material, such as aluminum, or is divided into sections interconnected by spring loaded hinges.

Harris et al. U.S. Pat. No. 5,769,804 issued Jun. 23, 1998 describes a laced wrist support comprising a preformed shell shaped to fit the patient's wrist with a thumb hole through the shell for receiving the wearer's thumb. An elastic tongue extends across the shell before being fully latched using a multi-strand lace extending over the elastic tongue. The multistrand lace is itself latched in place using a pair of self adhering hook and loop, fasteners.

Davini U.S. Pat. No. 5,385,537 issued Jan. 31, 1995 describes a wrist brace formed of semi-rigid material having a V-shaped cross section which cradles the wrist of the wearer. The semi-rigid brace is held in place by an attached flexible strap.

SUMMARY OF THE INVENTION

The invention relates to user wearable wrist supports and uses low temperature moldable, formable plastic, normally closed-cell foam, to replace the elastic material found in traditional wrist supports. This foam material is fabricated into the finished product using the improved method of the invention. The wrist support comprises a curvate clasp having a generally C shaped cross section, with the clasp encircling the wrist of the wearer. The clasp is secured by a strap, which may be formed during the wrist support fabrication.

In fabricating the wrist support, the material for forming the wrist support clasp is first prepared by forming a laminated composite material. The laminated composite material preferably comprises a flat sheet of a compressible heat formable closed cell foam, which is sandwiched between surface sheets of fabric. The fabrics are adhesively or otherwise attached to the sheet foam. The foam may be formed of any of a number of suitable synthetic materials, such as polypropylene, urethane, polyurethane, olefin, polyolefin, and similar materials. One example of such a material is a polyolefin film marketed under the trademark VOLARA.

The composite fabric-foam-fabric laminate is next clipper cut, die cut, or otherwise cut to the desired clasp body shape to create an uncompressed clasp body blank. The body blank is then subjected to selective compression and heat molding and forming into the desired C shape. It is in the nature of the closed cell foam of which the clasp is formed that it will retain its formed shape and density after the heat and pressure are removed. The compression is selectively applied, to provide in the C shaped body portion a sufficiently high density to furnish the desired flexible rigidity to hold the C shape. At the same time, according to one embodiment, the compression step provides more compression to create a securing tab or strap and an recess to receive the tab along with hook and loop securing material. The mold and compression are also such as to create an channel which receives a palmar stay.

In one embodiment of the method of the invention the stay is placed in position on the surface fabric on the uncompressed foam body blank. The positioned stay is then covered with a piece of cloth or fabric, and this fabric is sewn to the surface fabric to enclose the stay and hold it in position. The compression, heat treatment and molding then create the stay channel and fix the stay to the now formed clasp. The combination of the stay and the palmar support piece which covers it disposes the wrist and hand in the desired neutral or 15 degree position. In contrast to traditional wrist supports, the back of the hand is not covered by the support or restrained or immobilized.

In an alternative embodiment, the stay channel is defined by a pair of spaced parallel supports, which together form a channel between them. The stay is then positioned and secured at the bottom of the support flanked channel. The supports on either side of the stay perform the dual function of supporting the hand for keyboarding, while defining the channel which receives the palmar stay, which also provides support. The invention may further utilize an optional palmar strap to secure the palm and back of the hand to the palmar support piece, without imposing objectionable restraint on the hand motion necessary for comfortable keyboarding. The device of the invention is capable of performing the simultaneous functions of supporting the hand in the neutral position in the manner of a conventional stationary wrist rest for keyboarding, while at the same time providing carpal tunnel support for other activities in the manner of a carpal tunnel brace, all without imposing undue restraint on free hand motion.

According to a still further preferred embodiment of the invention the wrist support is formed from layered sheets of foam material which are of different hardness. The outer foam layer is of a higher density and is harder and more rigid than the softer and more flexible inner foam layer, which is in contact with the skin of the wearer. The outer layer is preferably formed of a material such as the previously mentioned polyolefin Volara, and is molded into a self supporting wrist encompassing bracelet or support having a generally C shaped cross section. The palmar stay is sandwiched between the outer and inner layers, which are attached to one another, such as by stitched edging. Additional stitching may be used around the periphery of the stay to secure it in position. This provides for a completely embedded palmar stay which is invisible to and is never brought into contact with the wearer. At the same time, the harder outer layer provides the desired self supporting rigidity to the curvate shape of the support.

A principle object of the present invention is to provide a wrist support directed to ensuring a neutral hand position of 15 degrees at all times when worn, as opposed to the stationary keyboard wrist rest, which works only when being used.

A further object of the present invention is to permit full finger dexterity because the back of the hand is not covered to the extent encountered with traditional wrist supports.

It is a further object of the invention to provide to the wearer of the wrist support a convenient means for customizing it to suit his or her preference. To this end a malleable, bendable, metal stay is incorporated in the product, and permits the user to increase or decrease the angle of support, unlike fixed keyboard wrist rests.

It is yet another object of the invention to eliminate the need for using both a stationary keyboard wrist rest and a worn wrist support, by uniquely incorporating the benefit of both products into one. This also eliminates the need for multiple keyboard wrist rests typically used by an individual. As a result of these combinations and eliminations, a significantly more functional and cost effective product is provided.

It is a further object of the invention to provide a method of fabricating a wrist support by cutting wrist support body blanks from a sheet of thermosetting foam laminated with fabric, selectively compressing at least one of the cut body blanks to form a compressed wrist support body having a tab integrally protruding from a first end portion, and having adjacent a second end of the body opposite to the first end an indentation to receive the tab, bending the body into an arcuate shape, and subjecting the bent body to heat so that it retains an arcuate shape.

It is yet another object of the invention to provide a wrist support which supports the hand of the wearer in a neutral position but permits unencumbered use of the hand.

It is a further object of the invention to provide a wrist support of the foregoing type having a stay and palmar pad which extend toward the palm substantially no farther than the heel of the hand.

It is another object of the invention to provide a self supporting C-shaped wrist support having a relatively hard surfaced outer layer, imparting the self support, and a relatively soft inner layer of a considerable thickness in contact with the wearer, the outer and inner layers having embedded therebetween a hidden stay controlling the position of the hand of the wearer.

It is yet another object of the invention to provide improved methodology for producing the wrist supports of the invention.

DESCRIPTION OF THE DRAWINGS

Further objects and advantages of the present invention will become apparent as the following description of illustrative embodiments proceeds, taken in conjunction with the accompanying drawings in which.

DESCRIPTION OF THE PREFERRED EMBODIMENT

Figures 1, 2:
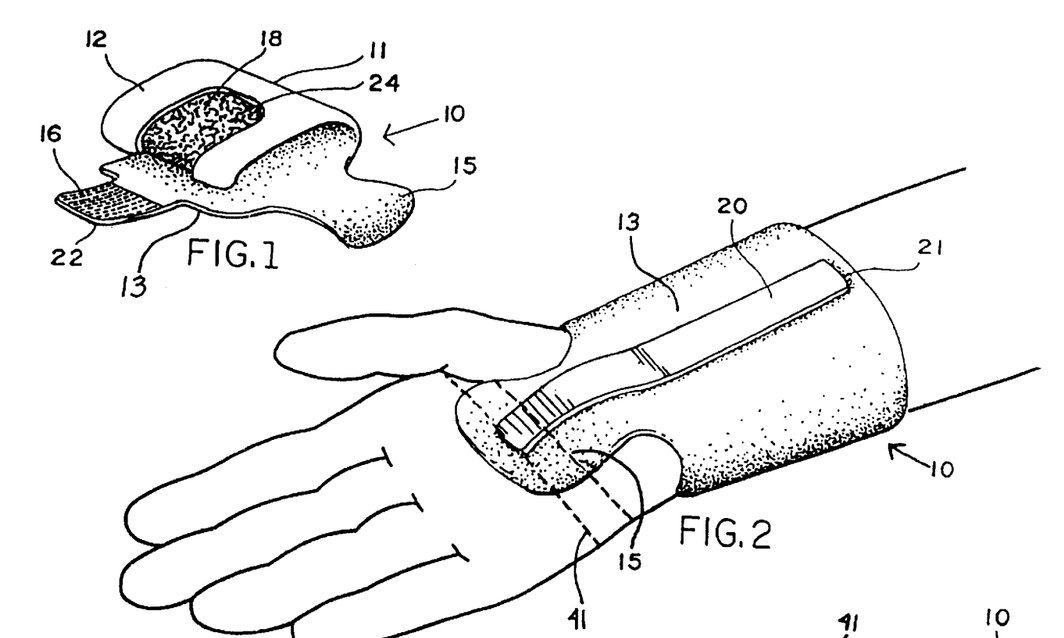
FIG. 1 is a perspective top or back of the hand view of one embodiment of the wrist and hand support of the invention showing its arcuate generally C shaped self supporting form in an open condition, prior to mounting on the wrist of a wearer.
FIG. 2 is a bottom or palm of the hand perspective view of the same wrist and hand support mounted on a wearer's wrist and hand, showing the hand in a palm upward orientation, and showing the palmar stay and optional palmar strap in phantom, as indicated by broken lines.

A first preferred embodiment of the invention is shown as a wrist support 10 in FIGS. 1 and 2. The wrist support comprises a clasp or body portion 11, which is C-shaped in cross section when in a unsecured condition, as seen in FIG. 1. The body portion has a back of the hand or dorsal side 12 and a palmer of the hand or ventral side 13. The palm side 13 has an integral palmar pad 15 extending from its edge. The palm pad has a width which is minimal at its connected end and maximum at its distal end.

Extending from one side of the open edge of the palm side in FIG. 1 is an integral securing tab or strap 16. The tab 16 is integral with the body portion 11 and is preferably of a lesser thickness than the remainder of the C shaped clasp. The tab 16 is formed to be received in a tab recess 18 which is provided in the top of the clasp 11 as seen in FIG. 1. Hook and loop linings 22 and 24 are secured to the tab 16 and in the recess 18. According to one embodiment of the invention the depth of the recess and thickness of the tab are chosen such that the top of the tab is flush with the surface of the body portion when it is received in the recess to secure the wrist support on the wrist of a wearer. While this integral tab feature comprises one embodiment of the invention, other strap closure arrangements may be used pursuant to the invention. A closure strap may be sewn or otherwise fastened to one side of the body portion and fastened by hook and loop securement to the other side. Still other strap closure equivalents will be apparent to those skilled in the art.

Referring to FIG. 2, a palmar stay 20 is positioned in a stay channel 21, which is formed in the outer surface of the palm side of the body portion during the compression, heat treatment and molding. The stay 20 is formed of a malleable, bendable material, such as aluminum or iron, and has a curvate end received in the channel 21 in the outside surface of the palm pad 15. The curvate end of the stay is concave toward the palm of the hand of the wearer to accommodate the heel of the hand and terminate in a distal end bent inwardly toward the palm. The stay determines the angle of the wrist and hand and is intended to maintain the preferred neutral position at 15 degrees. Because the palmar stay is malleable the user of the wrist support may make adjustments in its angle to suit the preferences of the wearer or a supervising medical advisor. The hand and wrist are shown in the preferred neutral position in FIG. 3. It can be seen that the end of the stay maintains the palmer pad 15 at the proper upwards angle.

Figure 3:
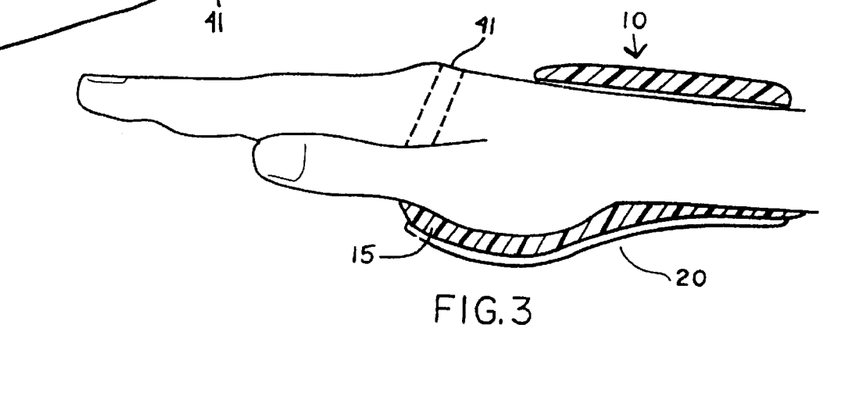
FIG. 3 is a longitudinal view, partly in section, showing the assembly of FIG. 2, and showing the optional palmar strap in phantom indicated by broken lines.
Figure 4:
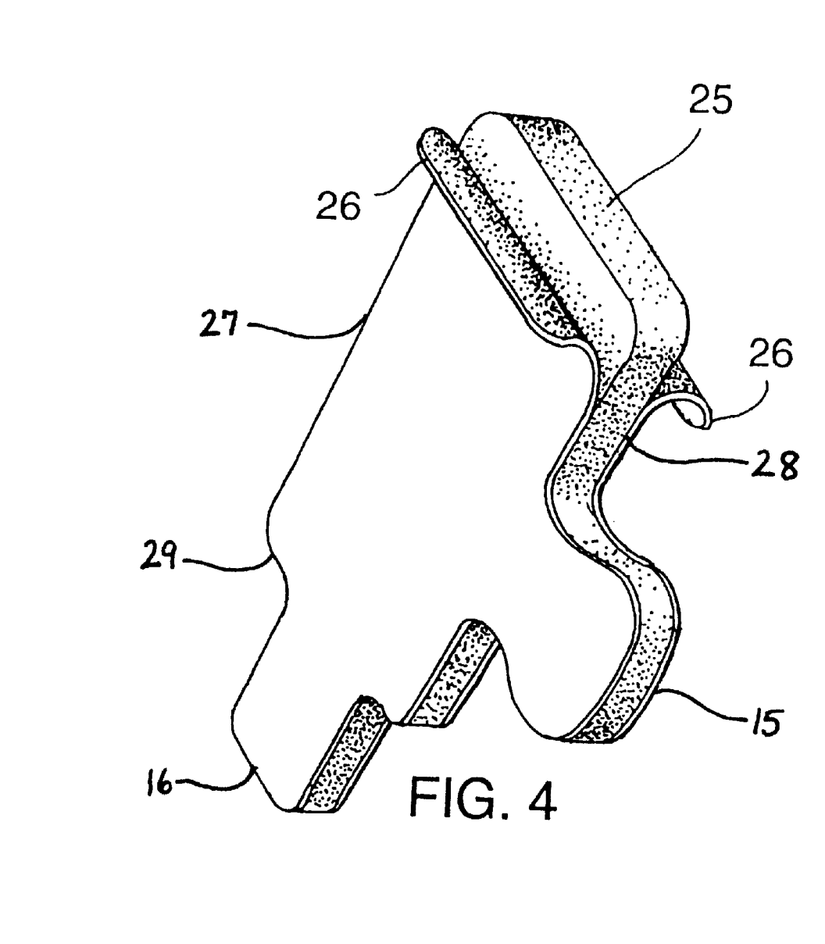
FIG. 4 is a perspective partially exploded view of an uncompressed blank for the fabric laminated body portion of the product of the invention illustrating the compressible heat formable foam core and its fabric exterior after cutting to shape, but before heat forming and compression.
Figure 5:
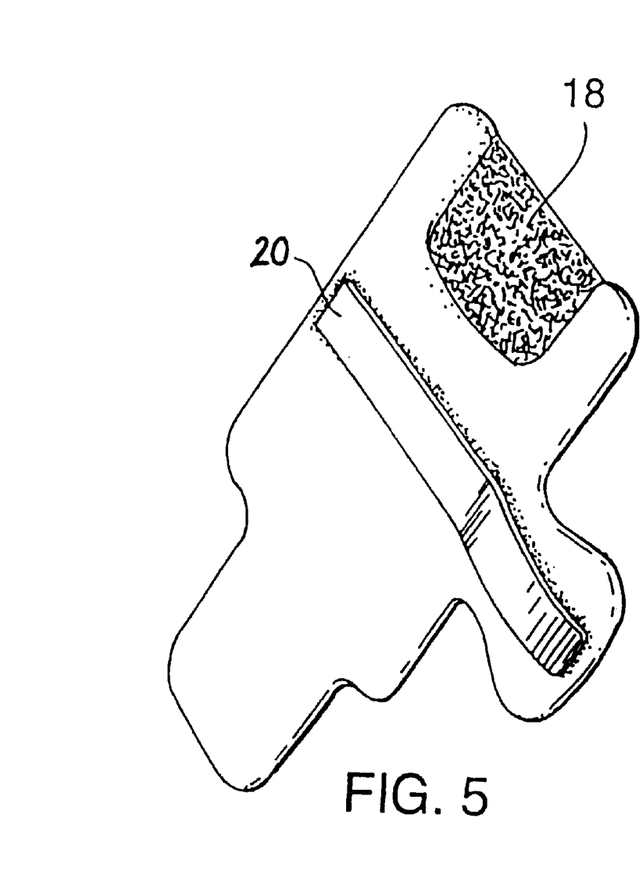
FIG. 5 is a flattened projection of the body portion of one embodiment of the wrist support which is formed from the blank shown in FIG. 4, after heat forming according to the invention. This flattened projection illustrates the palmar stay mounted in the stay channel which is formed in the molded foam body, according to one embodiment of the invention. The normal shape of the molded support body is curvate with a C-shaped cross section.

Turning now to FIGS. 4 and 5, there is seen in FIG. 4 a blank of uncompressed foam which has been cut to shape to make a wrist support of the type seen in FIGS. 1, 2, and 3. The blank is formed with a core 25 of foam to which a surface fabric 26 is laminated on both sides. The foam comprises a flat sheet of a compressible heat formable closed cell foam, which is sandwiched between surface sheets of fabric. The fabrics are adhesively or otherwise attached to the sheet foam. The foam may be formed of any of a number of suitable synthetic materials, such as polypropylene, urethane, polyurethane, olefin, polyolefin, and similar materials. Preferably, the foam may be molded at a temperature not exceeding 200 degrees F. One example of such a material is a polyolefin film marketed under the trademark VOLARA. VOLARA can be obtained from the Voltech Division of Sekisui American Corporation located in Lawrence, Mass. 01843. The fabric is not critical and may be of woven vinyl. Other fabrics having similar softness and wear characteristics are acceptable.

The wrist support body blank shown in FIG. 4 is of a thickness in excess of that desired in the finished product seen in FIGS. 1–3. It is to be understood that the drawings are not intended to be to scale. When the blank is in its premolded substantially planar form it has an oblong or substantially rectangular shape with two longer edges 28 and 29. The palmar pad 15 extends from the longer edge 29 in FIG. 4. The optional tab 16 extends from the left edge 29 in FIG. 4. The blank is subjected to selective compression and forming into the desired self supporting C or bracelet shaped form shown in FIG. 1. The compression is selectively applied, to provide in the C shaped body portion a sufficiently high density to furnish the desired flexible rigidity to hold the self supporting C shape. At the same time the compression and molding also provide compression and molding sufficient to create the securing tab 16 and the recess 18 to receive the tab and the hook and loop securing material, according to this particular embodiment of the invention. The molding and compression are also such as to create the channel 21 to receive the palmar stay 20.

The rectangular body portion of this embodiment of the invention is generally of a substantially uniform density over its major portion. According to a preferred embodiment of the method, the palmar stay 20 is sewn to the surface fabric on the blank prior to compression and molding. To this end the outermost surface of the stay may be covered with fabric which is sewn to the surface fabric on the foam. The stay may also be secured to the body portion of the wrist support by adhesive. Alternatively, the stay may be mounted after the molding step. As is explained in detail hereinafter, according to another embodiment of the invention the stay is positioned and embedded between two layers of foam, one of which has been molded into a self supporting C shaped form.

According to one embodiment the wrist support may optionally utilize a palmer strap 41 to secure the palm to the palmar pad 15, as indicated by broken lines in FIGS. 1 and 2. The palmar strap 41 is preferably attached to the to the palmar pad 15 adhesively or otherwise. This attachment is preferably to the outside surface of the palmar pad but may alternatively be to the inside surface. Alternative embodiments may utilize a palmar strap that is not attached to the body portion of the wrist support or is attached to the palm side of the palmar pad. The palmar strap may be of the conventional type which is securable to itself by a hook and loop attachment.

Figures 6, 7, 8, 9:
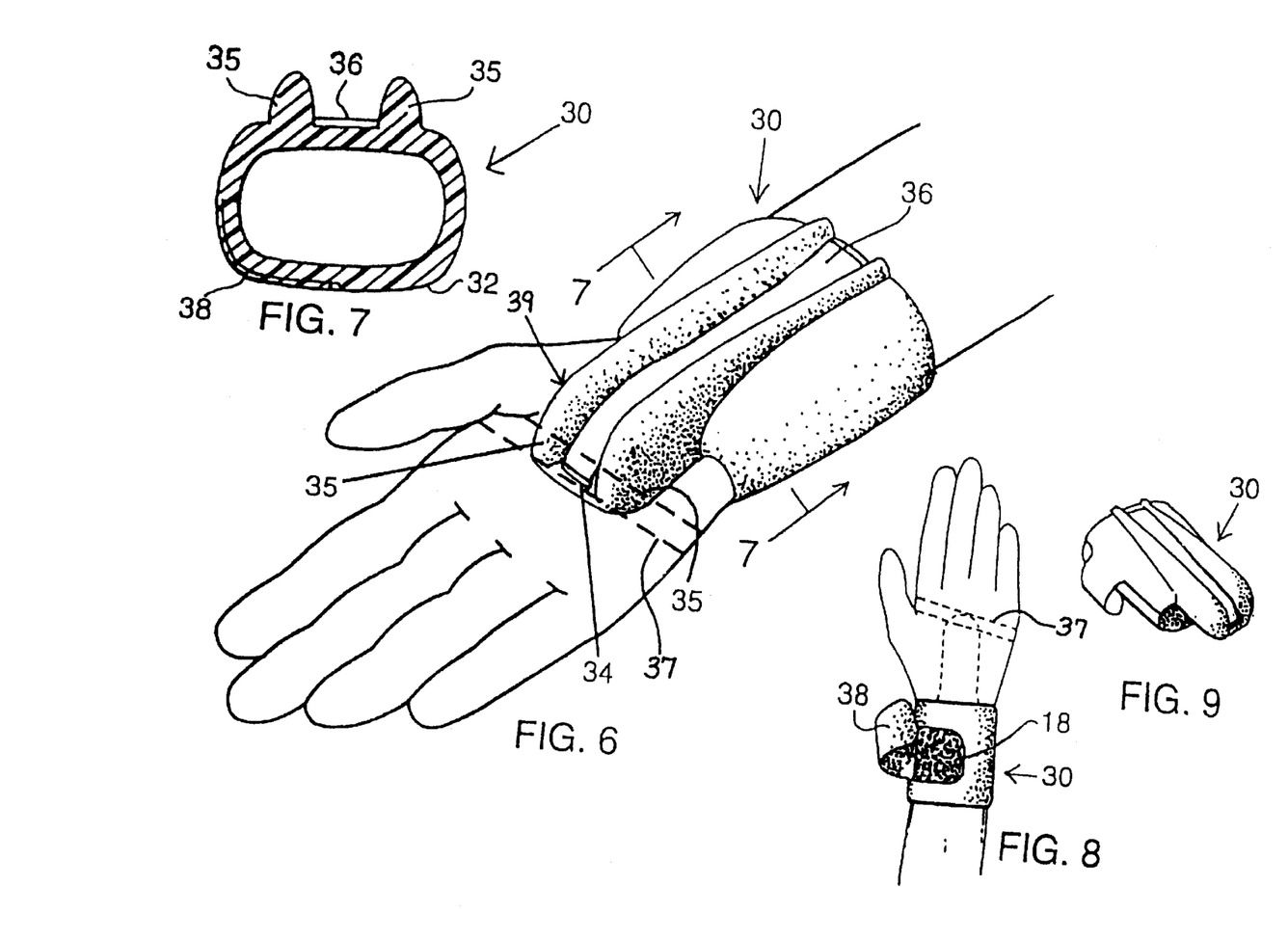
FIG. 6 is a perspective view of an alternative embodiment of the device of the invention mounted on a wearer, and shown with the palm facing upwardly. This illustrates the alternative embodiment having support pads flanking the palmar stay in the support piece, with the stay channel between the support pads.
FIG. 7 is a transverse sectional view taken along section line 7—7 of FIG. 6, illustrating the wrist encircling nature of the body of the unit in a secured position.
FIG. 8 is a view of the back of the hand showing the integral securing tab prior to engagement with its mating hook loop material indented below the outer surface of the body of the wrist encircling portion of the unit.
FIG. 9 is an perspective view of this embodiment of the device of the invention shown in a palm up orientation, such as that shown in FIG. 6, illustrating the securing tab before fastening.

Another embodiment of the invention is shown in FIGS. 6–9 and 11. Referring to these figures, this embodiment is best illustrated in FIG. 6. There it will be seen that the wrist support indicated generally at 30 has a clasp body 32, which surrounds the wrist, as is best shown in the sectional view of FIG. 7. According to this embodiment of the invention the wrist support is also provided with means to supply table surface support, much in the manner of the support provided by stationary wrist supports. This is particularly advantageous to wearers engaged in steady day-to-day keyboarding. Such wearers tend to become reliant upon conventional wrist support type assistance and yet need the additional support during the time that they are away from the keyboard.

Referring most particularly to FIGS. 6 and 7, there is shown a support generally similar to that illustrated in FIGS. 1–5. The wearer's wrist is surrounded by the body portion 32, which is secured in position by the integral tab or strap 38. As in the preceding embodiment, this tab is fastened by hook and loop fastening in a recess 18 to present a smooth exterior surface.

Figure 10:
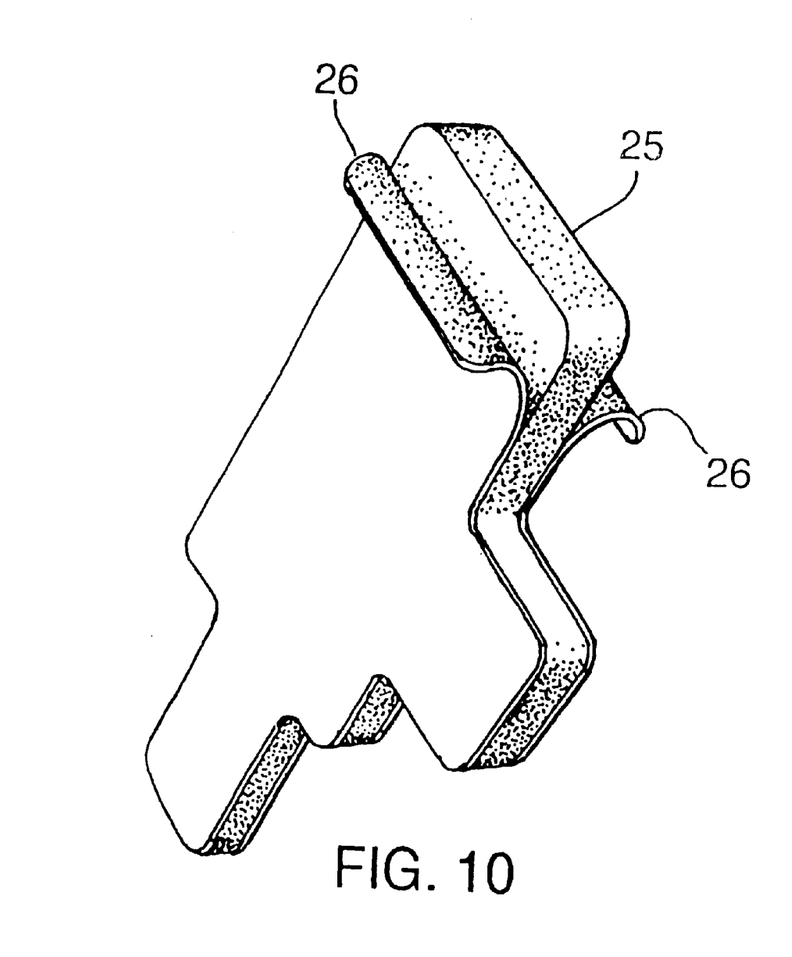
FIG. 10 is a view similar to that shown in FIG. 4, illustrating an uncompressed blank of laminated foam material for the embodiment of the invention shown in FIGS. 6–11.
Figure 11:
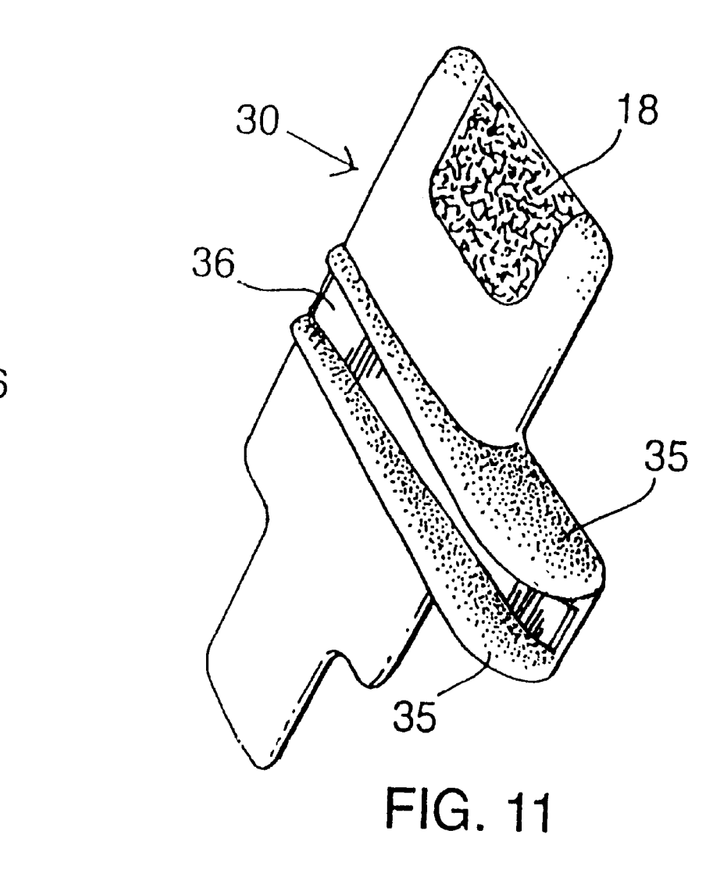
FIG. 11 is a view of the blank of laminated foam material of FIG. 10 after heat treatment, compression and forming into the embodiment of the device of the invention shown in FIGS. 6–11.

However, unlike the prior embodiment of the invention, there are here provided two elongated supports 35 which extend across the clasp and onto the palmar pad 39. These parallel supports are spaced and define between them a palmar stay channel 34 which receives the stay 36. As with the prior embodiment, the stay 36 may be secured by a cloth or fabric cover which is sewn to the fabric surface of the pre-molding blank shown in FIG. 10. Alternately the stay may be simply secured by adhesive.

The method of fabricating this embodiment of the invention is virtually the same as that used for the prior embodiment. However, with this embodiment of the invention the formation of the elongated supports 35 requires a more advanced mold form. The compression, heat and molding may be performed with the stay 36 in position, as was preferably done with the prior embodiment. Alternately the support may be formed and the stay later adhered within its channel. As with the prior embodiment, an optional palmar strap 37 may be used. However, with this embodiment of the invention the palmar strap 37 is preferably secured between the palm and the palm facing surface of the palmar pad 39. Other methods of attaching the palmer strap to the palmar pad may be used, as are known to practitioners in the relevant arts.

Figure 12:
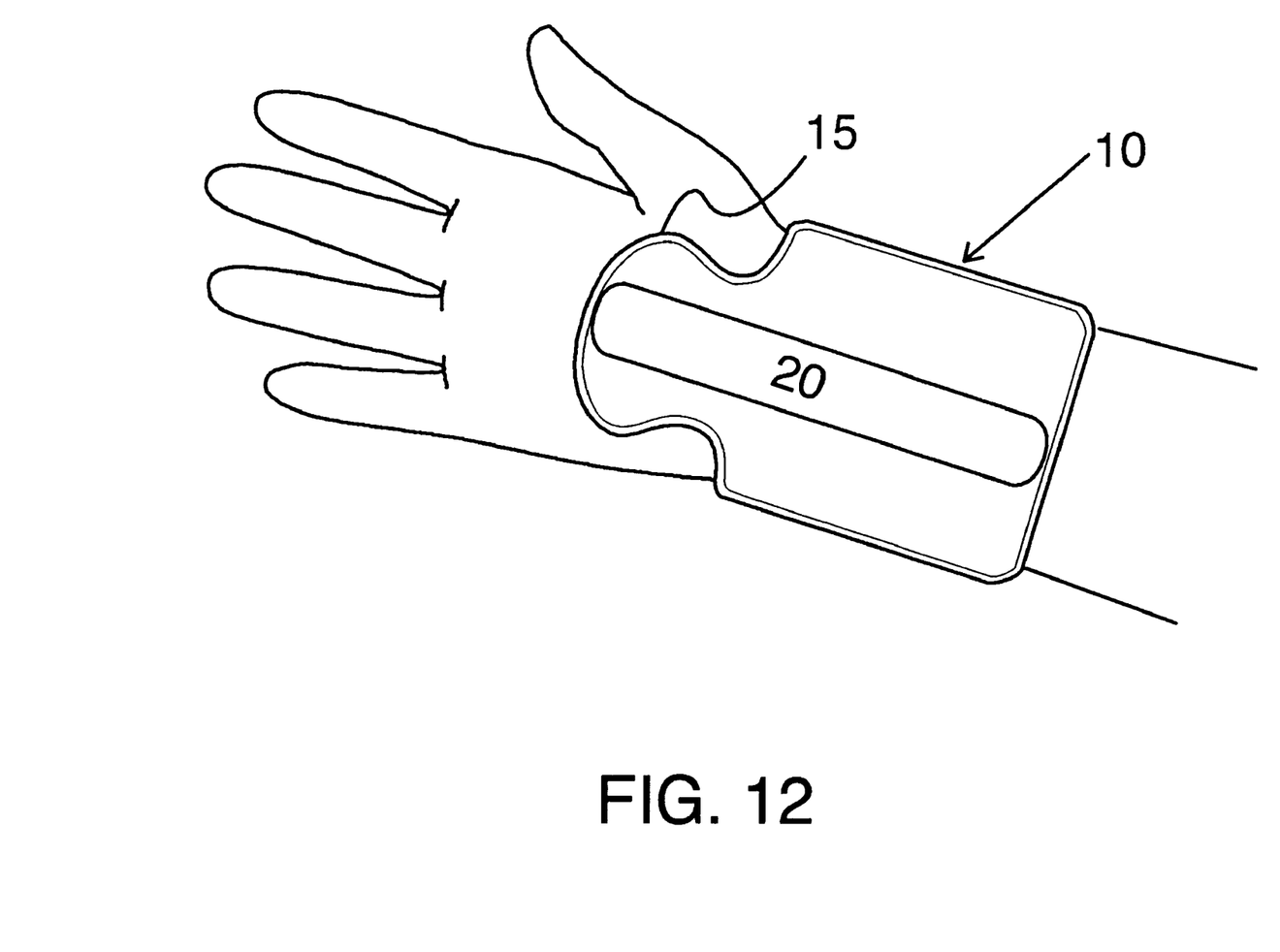
FIG. 12 is a perspective view illustrating a preferred embodiment of the invention in which the wrist support extends toward the center of the palm substantially no farther than the heel of the hand.

According to a yet further embodiment of the invention there is provided a wrist support which permits virtually completely unencumbered use of the hand while still maintaining the hand and wrist in the neutral position. It has been discovered that wrist support to maintain the hand in the desired neutral position may be provided by a palmar pad 15 and palmar stay 20 that extend substantially no farther than the heel of the hand. Such a wrist support is illustrated in FIG. 12. It has been found that a palm pad and stay that extend onto the heel of the hand are sufficiently beyond the effective axis of the wrist-hand joint to support the hand and wrist in the neutral position. This type of support provides the needed restraint but without the usual encumberment.

Figure 13:
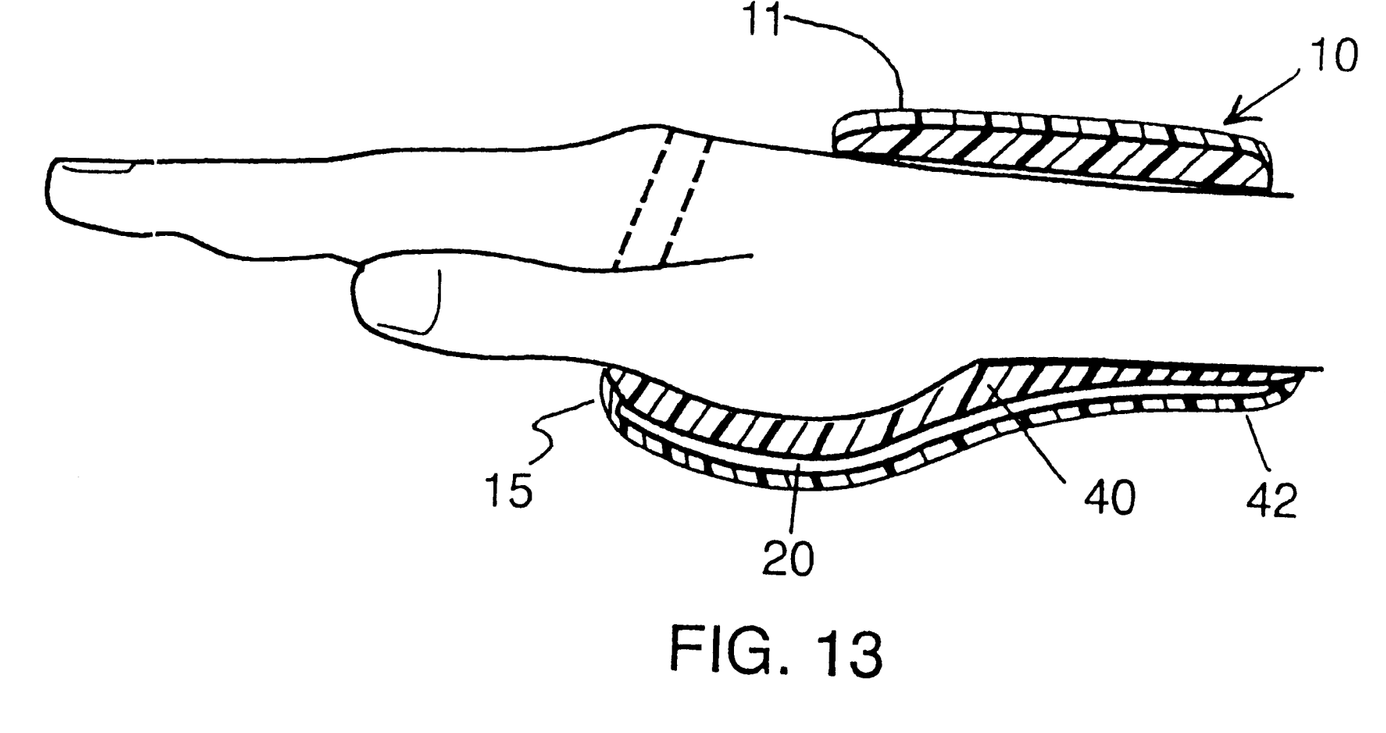
FIG. 13 is a side elevational view, partly in section, showing another preferred embodiment of the invention wherein the palmar stay is embedded between an outer layer of denser, harder material and an inner layer of softer foam material.

Referring to FIG. 13, there is illustrated a longitudinal view, partly in section, showing another embodiment of the invention. FIG. 13 is generally comparable to FIG. 3. In the embodiment of the invention shown in FIG. 13, the wrist support is comprised of two layers of foam material, an inner layer 40 of flexible, soft foam and an outer layer 42 of more dense, formed and molded foam, which provides self support to the composite support. The outer layer is molded while the inner layer is substantially in its cut blank form, which has not been subjected to molding. Preferably, the inner foam layer is of a thickness substantially in excess of the thickness of the fabrics sometimes used to provide an inner facing to sewn supports. This permits the soft compliant foam to be compressed under pressure from the wrist and hand of the user, and tends to provide a comfortable support, which is significantly independent of idiosyncrasies in the anatomy of the wearer.

In manufacturing a composite layered support of this type according to the method of the invention, the outer layer may be produced using the methodology previously described in connection with the single layer wrist support. Thus, the outer layer is provided by forming a blank such as shown in FIG. 4, and compressing and molding that blank into the self-supporting shape shown in FIG. 1. The blank is formed of the same type material utilized in the preceding embodiments of the invention.

The foam material which is to form the inner foam layer is also cut from a foam sheet of similar or equivalent material, into a blank of the type shown in FIG. 4, which is then mounted within the formed outer layer. The inner layer remains in its soft foam condition and is fastened to the harder outer layer by stitching or stitched edging. The stay 20 is positioned between the two layers 40, 42 before fastening them together, and may be secured in position by stitching through the two layers around the periphery of the stay. This technique eliminates cutting and sewing an independent stay cover and retainer. Both the inner and outer layers of the wrist support 10 are preferably surfaced with fabric, at least at the exposed surfaces thereof. Thus the inner layer is surfaced with fabric on the inside of the support, and the outer layer is surfaced with fabric on the outside surface of the support. Edging material (not shown) may be sewn around the edges of the support in a known manner. The stay is embedded in the support out of sight of the wearer.

It will be readily seen by one of ordinary skill in the art that the present invention fulfills the objects and objectives set forth above. After reading the foregoing specification, one of ordinary skill will be able to effect various changes, substitutions of equivalents and to vary other aspects of the invention as broadly disclosed herein. It is therefore intended that the protection granted hereon be limited only by the definition contained in the appended claims and equivalents thereof.

What is claimed is:

1. A wrist support comprising a wrist support body formed from an oblong blank of synthetic resin which has been compressed and heat molded into a self-supporting arcuate shape having a generally C-shaped cross section,
    an integral palmar pad extending transverse of said oblong body from an edge thereof, and having a stay channel extending transverse of said oblong body and into said integral palmar pad,
    a malleable stay mounted in said stay channel for supporting said integral palmar pad against the palm of a wearer, and
    a strap extending around at least a portion of the outer periphery of said C-shaped cross section to adjustably and releasably secure said support body around the wrist of a wearer.

2. A wrist support comprising a clasp body of molded heat formable synthetic resin foam having a longitudinal axis;
    an integral palmar pad extending generally parallel to said axis from one edge of said clasp body and carrying a palmar stay, said stay also extending from said edge generally across said clasp body;
    a strap secured to said clasp body and extending circumferentially around at least a portion thereof to releasably fasten said clasp body on the wrist of a wearer; and
    whereby said wrist support supports the hand of the wearer in a predetermined position.

3. A wrist support according to claim 2 wherein said clasp body has a generally self supporting C shaped cross section along said longitudinal axis, and said palmar pad and said palmar stay extending from said edge in a direction to overlie the hand of a wearer when said clasp body encircles the wrist of the wearer.

4. A wrist support according to claim 3 wherein said palmar pad being adapted to extend into the palm of a wearer only so far that said palmar pad covers the heel of the hand.

5. A wrist support according to claim 4 wherein said molded thermoplastic foam has attached thereto an inner layer of foam material of a lesser density and hardness.

6. A wrist support according to claim 2 wherein said stay and palmar pad are curvate to position the hand of a wearer in a predetermined neutral position.

7. A wrist support comprising a clasp body having a distal end and a proximal end, said proximal end being terminable at the forearm of a wearer and said distal end being configured to terminate no farther than the wrist-heel junction of the wearer;
    an integral palmer pad extending from the distal end capable of at least partially covering the palm of the wearer and terminable no farther than the palm fold of the hand;
    a palmar stay attached to said palmer pad and to said clasp and configured to be disposed away from the wearer, said palmar stay being generally linear along a longitudinal axis and a transverse axis and curvilinear in a direction normal to said axes such that said palmar stay is configured to be bent downwards at the wrist-heel junction to prevent dropping of the wrist, bent upwards to support the hand in a neutral position, extend at least partially across the heel of the hand and terminate no farther than the heel of the hand; and
    a strap having a first end secured to said wrist support and a second end releasably attachable to said wrist support.

8. A wrist support according to claim 7 wherein said wrist support being adapated to not cover or restrain the back of the hand or the thumb of the wearer.

9. A wrist support according to claim 8 wherein said wrist support has one strap.

10. A wrist support according to claim 7 wherein said stay being configured to generally follows the contour of the heel of the hand.

11. A wrist support according to claim 7 wherein the neutral position is about 15 degrees.

12. A wrist support according to claim 7 wherein said clasp body is sufficiently rigid to be self-supporting and said clasp body is conformable to the contour of the forearm of the wearer.

13. A wrist support according to claim 12 wherein wrist support is adapted to flushly conform against the wrist-heel junction and wherein said clasp body is adapted to separate said stay from the wearer.

14. A wrist support according to claim 12 wherein said palmer pad being configured to support the wearer at the center of the hypothenar eminence and at the center of the thenar eminence such that the hypothenar eminence and the thenar eminence are restricted from moving towards each other.

15. A method for supporting a wrist of a wearer with a wrist support comprising the steps of:
    providing a clasp body having a distal end and a proximal end, said proximal end terminating at the forearm of a wearer and said distal end terminating no farther than the wrist-heel junction of the wearer;
    providing an integral palmer pad extending from the distal end and terminating substantially no farther than the heel of the hand;
    providing a palmar stay attached to said palmer pad and to said clasp and disposed away from the wearer, said palmar stay is generally linear along a longitudinal axis and a transverse axis and is curvilinear in a direction normal to said axes such that said palmar stay is bent downwards at the wrist-heel junction to prevent dropping of the wrist, bent upwards to support the hand in a neutral position and terminates no farther than the heel of the hand;

providing a strap having a first end secured to said wrist support and a second end releasably attachable to said wrist support;

supporting the hand in a neutral position when the hand is resting against said palmar pad; and permitting the hand to move unrestricted upwards away from the neutral position when the wrist support is attached to the hand.

\* \* \* \* \*